(12) United States Patent
Wendland et al.

(10) Patent No.: US 10,814,071 B2
(45) Date of Patent: Oct. 27, 2020

(54) DRUG DELIVERY DEVICE WITH PROTECTIVE NEEDLE CAP CONTROL AND DEVICE ACTIVATION MECHANISM

(71) Applicant: SANOFI-AVENTIS DEUTSCHLAND GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 87 days.

(21) Appl. No.: 15/743,840

(22) PCT Filed: Jul. 13, 2016

(86) PCT No.: PCT/EP2016/066585
§ 371 (c)(1),
(2) Date: Jan. 11, 2018

(87) PCT Pub. No.: WO2017/009360
PCT Pub. Date: Jan. 19, 2017

(65) Prior Publication Data
US 2018/0200453 A1    Jul. 19, 2018

(30) Foreign Application Priority Data

Jul. 15, 2015  (EP) .................................. 15176870

(51) Int. Cl.
*A61M 5/32* (2006.01)
*A61M 5/31* (2006.01)
*A61M 5/162* (2006.01)

(52) U.S. Cl.
CPC ........ *A61M 5/3204* (2013.01); *A61M 5/3243* (2013.01); *A61M 5/3257* (2013.01);
(Continued)

(58) Field of Classification Search
CPC .............. A61M 5/3204; A61M 5/3257; A61M 2005/312; A61M 5/326
See application file for complete search history.

(56) References Cited

U.S. PATENT DOCUMENTS

| | | | |
|---|---|---|---|
| 2005/0096599 A1 | 5/2005 | Crawford et al. | |
| 2013/0281937 A1 | 10/2013 | Limaye | |
| 2016/0015896 A1* | 1/2016 | Cowe ................ | A61M 5/31571 604/198 |

FOREIGN PATENT DOCUMENTS

| | | |
|---|---|---|
| EP | 2361648 | 8/2011 |
| JP | 2003-523804 | 8/2003 |

(Continued)

OTHER PUBLICATIONS

International Preliminary Report on Patentability in International Application No. PCT/EP2016/066585, dated Jan. 16, 2018, 8 pages.

(Continued)

*Primary Examiner* — Nathan R Price
*Assistant Examiner* — Melissa A Snyder
(74) *Attorney, Agent, or Firm* — Fish & Richardson P.C.

(57) ABSTRACT

A drug delivery device includes an outer body receiving a cartridge with a needle, a needle cap adapted to be coupled to the outer body and to cover the needle and a control mechanism for activating the drug delivery device. The control mechanism includes a control element received within the outer body and axially and/or rotationally movable relative to the outer body between an initial position, a first activating position, and a second activating position. The control element is coupled to the needle cap and to the cartridge, the needle cap is retained on the outer body when the control element is in the initial position, the needle cap is released from the outer body and the needle is covered by the outer body when the control element is in the first
(Continued)

activating position, and the needle is exposed when the control element is in the second activating position.

16 Claims, 4 Drawing Sheets

(52) U.S. Cl.
CPC ..... *A61M 5/1626* (2013.01); *A61M 2005/312* (2013.01); *A61M 2005/3208* (2013.01); *A61M 2005/3252* (2013.01)

(56) References Cited

FOREIGN PATENT DOCUMENTS

| | | |
|---|---|---|
| JP | 2015/047478 | 3/2015 |
| WO | WO 01/54758 | 8/2001 |
| WO | WO 2009/040602 | 4/2009 |
| WO | WO 2011/101378 | 8/2011 |
| WO | WO 2013/089616 | 6/2013 |
| WO | WO 2014/131858 | 9/2014 |

OTHER PUBLICATIONS

International Search Report and Written Opinion in International Application No. PCT/EP2016/066585, dated Sep. 23, 2016, 11 pages.

\* cited by examiner

DRUG DELIVERY DEVICE WITH PROTECTIVE NEEDLE CAP CONTROL AND DEVICE ACTIVATION MECHANISM

CROSS REFERENCE TO RELATED APPLICATIONS

The present application is the national stage entry of International Patent Application No. PCT/EP2016/066585, filed on Jul. 13, 2016, and claims priority to Application No. EP 15176870.2, filed in on Jul. 15, 2015, the disclosures of which are expressly incorporated herein in entirety by reference thereto.

TECHNICAL FIELD

The disclosure relates to a drug delivery device.

BACKGROUND

Administering a medicament by injection is a process which presents a number of risks and challenges for patients and healthcare professionals, both mental and physical. Drug delivery devices typically fall into two categories—manual devices and autoinjectors. In a conventional manual device, manual force is required to drive a medicament through a needle. This is typically done by some form of button/plunger that has to be continuously pressed during the injection. Autoinjector devices aim to make self-injection easier for patients. A conventional autoinjector may provide the force for administering the injection by a spring, and a trigger button or other mechanism may be used to activate the injection. Autoinjectors may be single-use or reusable devices.

Improper handling of drug delivery devices may result in needle stick injuries. In any situation in which a patient or healthcare professional is required to manually remove a needle cap or needle assembly, there is a risk of needle stick injury.

Thus, there is a need for a drug delivery device with a control mechanism for safely preparing a drug delivery device for operation with a reduced risk for needle stick injuries.

SUMMARY

Aspects of the present disclosure relate to an improved drug delivery device comprising such a control mechanism.

According to the disclosure, a drug delivery device comprises an outer body adapted to receive a cartridge with a needle, a needle cap assembly adapted to be coupled to the outer body and to cover the needle, and a control mechanism for activating the drug delivery device. The control element comprises a control element that is received within the outer body and that is movable rotationally and/or axially relative to the outer body between an initial position, a first activating position and a second activating position, wherein the control element is coupled to the needle cap assembly and to the cartridge. Furthermore, the needle cap assembly is retained on the outer body when the control element is in an initial position, wherein the needle cap assembly is released from the outer body and the needle is covered by the outer body when the control element is in a first activating position, and wherein the needle is exposed when the control element is in a second activating position.

The control mechanism facilitates removal of the needle cap assembly from the drug delivery device and actuation of the drug delivery device using a single control mechanism, thereby improving the ease of use of the drug delivery device and the safety for a user of the device. The control element may be directly coupled to the needle cap assembly and to the cartridge. For example, the cartridge abuts against a stop on the control element.

In an exemplary embodiment, the control element comprises a single activating element operable from an outside of the outer body and adapted to move the control element relative to the outer body in order to subsequently release the cap assembly from the outer body and to expose the needle. This allows a user manually operating the control element. For example, the activating element is configured as a lever that may protrude radially outwards through a slot in the circumference of the outer body and may thus be gripped by a user.

The slot may be limited by a first stop and a second stop. For example, the slot extends in a circumferential direction of the outer body. In an exemplary embodiment, the activating element is guidable within the slot, wherein the activating element abuts the first stop in the initial position. Alternatively, the activating element abuts the second stop in the initial position.

In a further exemplary embodiment, the activating element is between the first stop and the second stop in the first activating position. The activating element is thus moved from the initial position into the first activating position until the activating element stops. For example, there may be a detent within the slot requiring a certain force for overcoming it.

In an exemplary embodiment, the activating element abuts the second stop in the second activating position.

In an exemplary embodiment, the control element is configured as an elongate sleeve arranged within the outer body and rotatably movable with respect to the outer body when the activating element is moved within the slot.

In a further exemplary embodiment, the control element is adapted to be screwed to the needle cap assembly, wherein the needle cap assembly may comprise an outer thread arranged proximally, and the control element may comprise a corresponding inner thread arranged distally. In an alternative embodiment, the needle cap assembly may comprise an inner thread arranged proximally, and the control element may comprise a corresponding outer thread arranged distally.

In an exemplary embodiment, when the control element is in the initial position, the needle cap assembly is rotationally locked to the outer body by a snap connection, wherein the outer body may comprise a number of locking projections on a distal end that engage into a number of corresponding recesses on the needle cap assembly. Thus, the needle cap assembly may be engaged to the outer body secured against unintended removal from the drug delivery device in the initial position of the activating element.

In an exemplary embodiment, the control element is mechanically coupled to the cartridge.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given herein below and the accompanying drawings which are given by way of illustration only, and thus, are not limitative of the present invention, and wherein.

Corresponding parts are marked with the same reference symbols in all figures.

DETAILED DESCRIPTION

Figure 1:
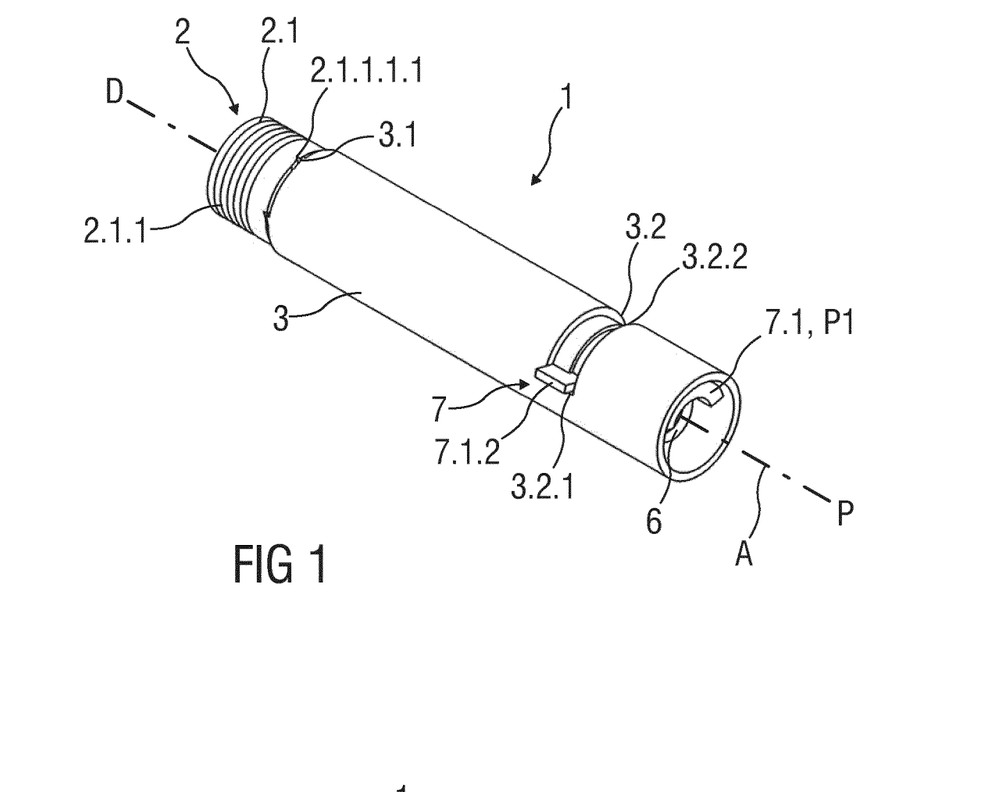
FIG. 1 is a schematic perspective view of an exemplary embodiment of a drug delivery device with a control mechanism including a control element in an initial position.
Figure 2:
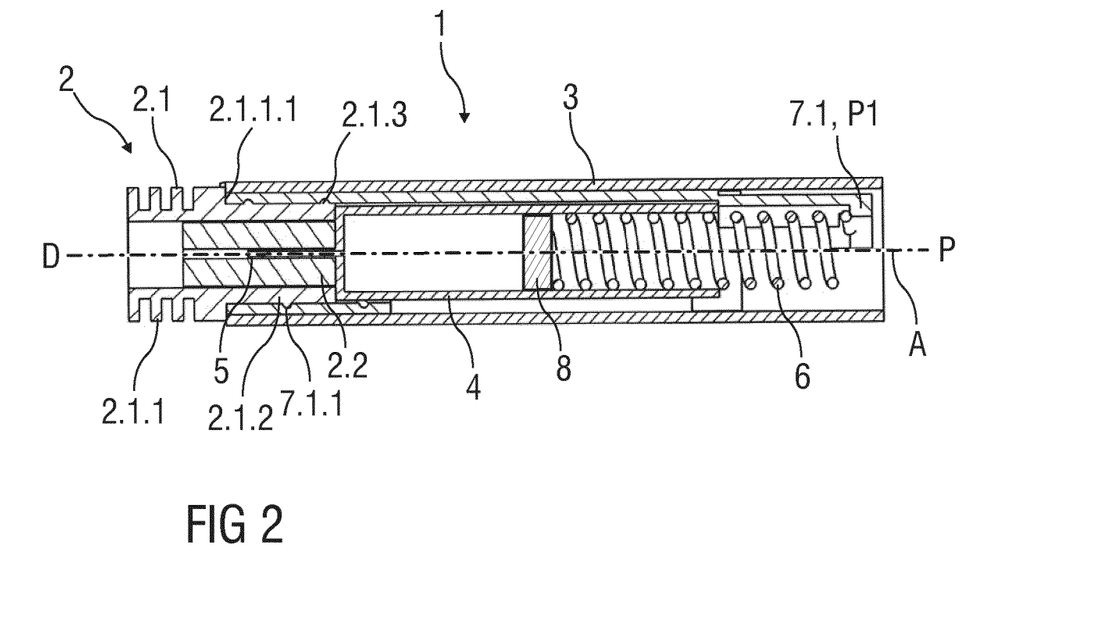
FIG. 2 is a schematic sectional view of the drug delivery device.

FIG. 1 shows a schematic perspective view of an exemplary embodiment of a drug delivery device 1 comprising a longitudinal axis A extending from a proximal direction P towards a distal direction D. FIG. 2 shows a longitudinal section of the drug delivery device 1 illustrated in FIG. 1.

The drug delivery device 1 further comprises a needle cap assembly 2, a sleeve-shaped outer body 3, a cartridge 4 with a needle 5, a drive spring 6 and a control mechanism 7 adapted to remove the needle cap assembly 2 and to trigger the drug delivery device 1 for starting a drug delivery process.

In the shown exemplary embodiment, the needle cap assembly 2 comprises a needle cap 2.1 and an inner needle shield 2.2 fixed within the needle cap 2.1. The needle cap 2.1 and the inner needle shield 2.2 may be joined together in a force-fit, form-fit and/or bonded connection. For example, the inner needle shield 2.2 is adhesively bonded to the needle cap 2.1.

The needle cap 2.1 comprises a distal portion 2.1.1 and a proximal portion 2.1.2. The distal portion 2.1.1 provides an ergonomic grip for a user's finger or fingers. A diameter of the distal portion 2.1.1 is greater than a diameter of the proximal portion 2.1.2, thus the distal portion 2.1.1 comprises a shoulder 2.1.1.1 abutting against a distal end of the outer body 3 as long as the needle cap assembly 2 is locked to the drug delivery device 1. The shoulder 2.1.1.1 further abuts against a distal end of a control element 7.1, which will be described below in more detail.

The shoulder 2.1.1.1 comprises a number of recesses 2.1.1.1.1 that corresponds with a number of locking projections 3.1 arranged on the distal end of the outer body 3 providing a snap connection between the needle cap assembly 2 and the outer body 3. Thus, the needle cap 2.1 is secured against unintended removal from the drug delivery device 1.

The proximal portion 2.1.2 is arranged within the outer body 3, wherein a proximal end of the proximal portion 2.1.2 abuts against a distal end of the cartridge 4 as long as the needle cap assembly 2 is locked to the drug delivery device 1. The inner needle shield 2.2 is received fixedly within the proximal portion 2.1.2 covering a distal tip of the needle 5. The inner needle shield 2.2 comprises a substantially cylindrical shape with a central opening for receiving the needle 5.

The cartridge 4 is arranged within the outer body 3 and the needle 5 is arranged proximally behind a distal end of the outer body 3 as illustrated in FIGS. 1 and 2. The cartridge 4 may be a prefilled syringe containing a liquid medicament. The needle 5 may be removably engaged with the distal end of the cartridge 4, e.g., by threads, snaps, friction, etc. Alternatively, the needle 5 may be fixed to the cartridge 4.

The cartridge 4 is coupled to the drive spring 6 and arranged to move relative to the outer body 3. In the shown exemplary embodiment, the drive spring 6 is configured as a coil spring having two ends, wherein a proximal end of the drive spring 6 is coupled to a proximal end of the control element 7.1 and a distal end of the drive spring 6 is coupled to a stopper 8 adapted for sealing the cartridge 4 in the proximal direction P and for displacing the medicament contained in the cartridge 4 through the needle 5. The stopper 8 may be displaced under a spring force upon release of the drive spring 6. In a further not shown exemplary embodiment, the drive spring 6 may be additionally coupled to a piston rod that comprises the stopper 8 on a distal end, wherein the piston rod is movable within the cartridge 4 under the spring force of the drive spring 6.

The control element 7.1 is a component of the control mechanism 7 which is arranged for removing the needle cap assembly 2 from the drug delivery device 1 and for triggering the drug delivery device 1 ready to start a drug delivery process.

Figure 7:
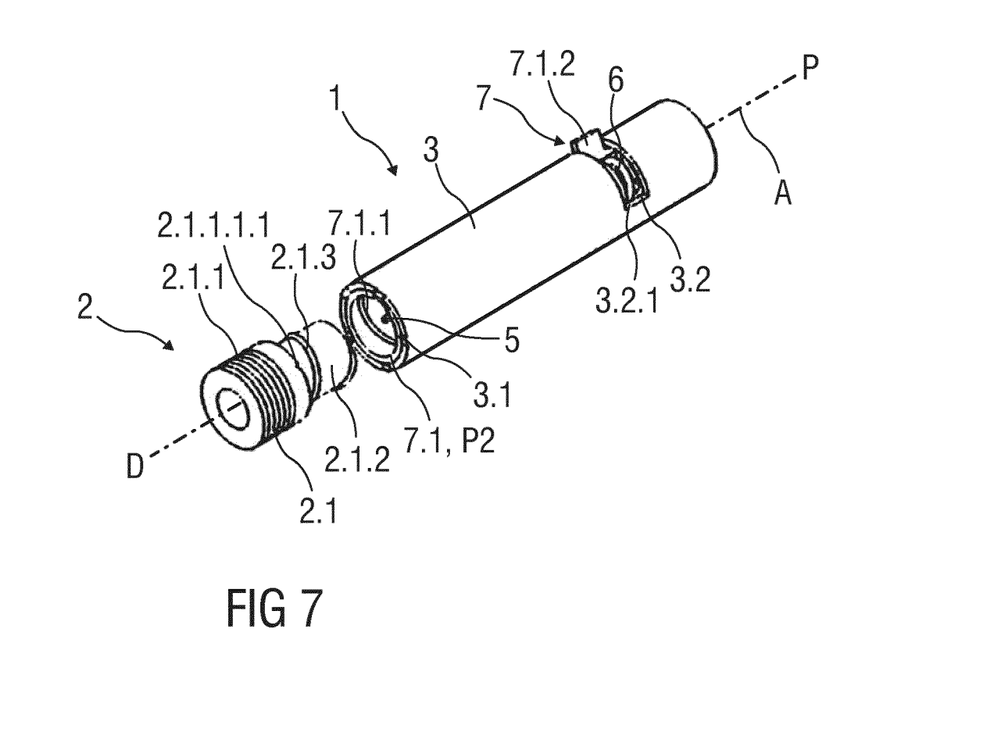
FIG. 7 is a further schematic perspective view of the drug delivery device.

The control element 7.1 is elongate and substantially sleeve shaped and is arranged rotatably within the outer body 3. On a distal end, the control element 7.1 comprises an inner thread 7.1.1 arranged on an inner circumference of the control element 7.1. The inner thread 7.1.1 is adapted to engage with an outer thread 2.1.3 arranged on an outer circumference of the proximal portion 2.1.2 of the needle cap 2.1. Thus, the control mechanism 7 provides a locking connection between the needle cap assembly 2 and the drug delivery device 1, wherein the needle cap assembly 2 is screwed to the control element 7.1. The distal end of the control element 7.1 abuts against the shoulder 2.1.1.1 of the needle cap 2.1 as described before. Due to the sleeve shape of the control element 7.1, the distal end of the control element 7.1 provides a circular abutting area for the shoulder 2.1.1.1 as illustrated in FIG. 7. Alternatively, the control element 7.1 may comprise a partial sleeve shape, thus providing an abutting area with two or more circular sections.

The control element 7.1 further comprises a activating element 7.1.2 projecting radially outwards through a slot 3.2 within the circumference of the outer body 3. The slot 3.2 extends in a circumferential direction and is limited by a first stop 3.2.1 and a second stop 3.2.2. The activating element 7.1.2 provides a gripping portion of the control element 7.1, e. g. the activating element 7.1.2 is configured as a lever, and is guidable within the slot 3.2, thereby manually movable between the stops 3.2.1, 3.2.2. In a not shown alternative embodiment, the activating element 7.1.2 may be arranged on a proximal end of the control element 7.1. Likewise, the activating element 7.1.2 may be configured additionally as a depressible button element.

As illustrated in FIGS. 1 and 2, the activating element 7.1.2 abuts against the first stop 3.2.1 which defines an initial position P1 of the activating element 7.1.2. In this initial position P1, the needle cap assembly 2 is locked to the drug delivery device 1 and the drug delivery device 1 is not ready for starting a drug delivery process.

Figure 3:
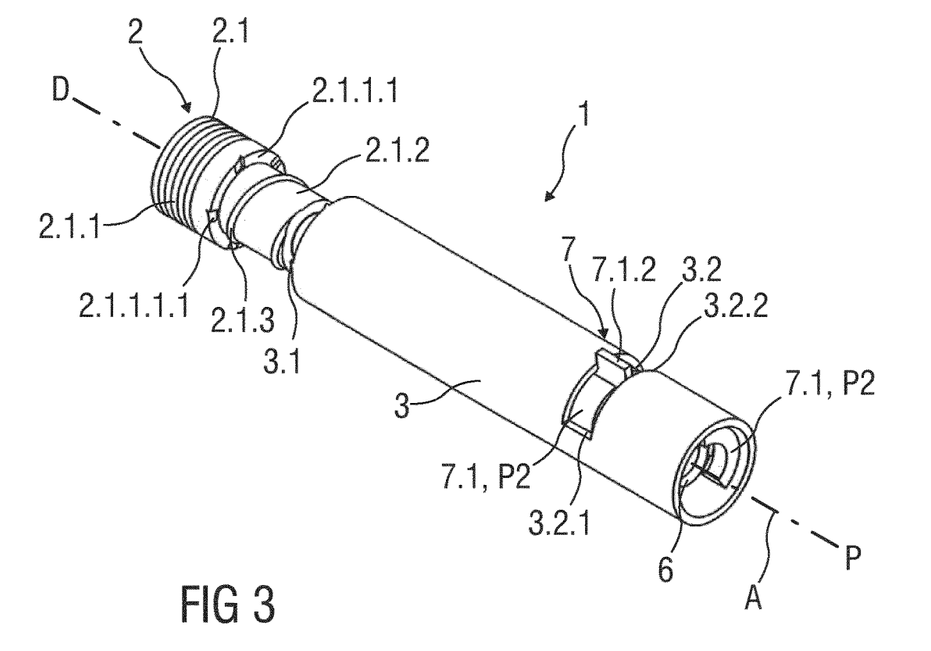
FIG. 3 is a schematic perspective view of an exemplary embodiment of the drug delivery device with the control element in a first activating position.
Figure 4:
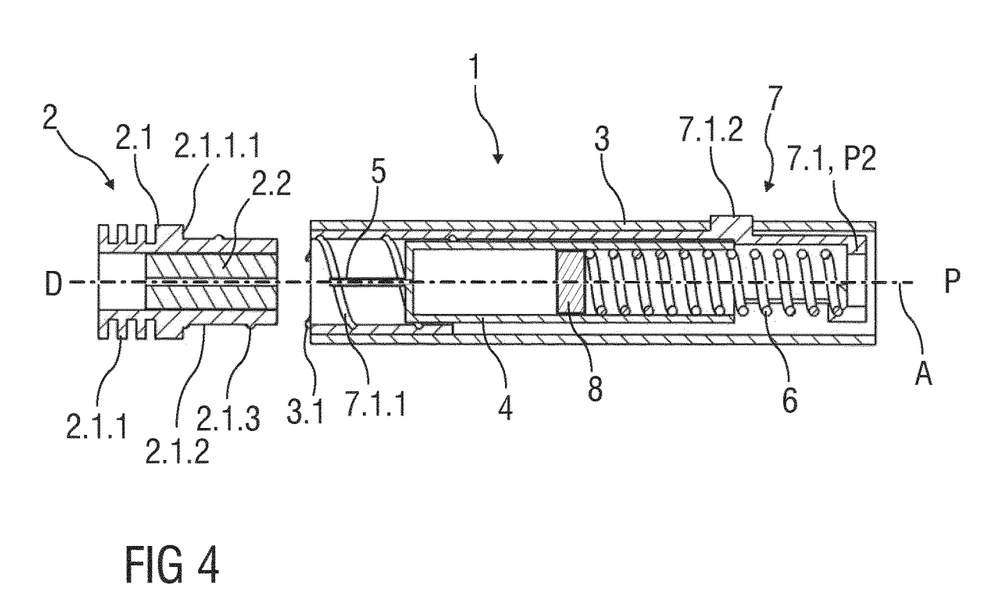
FIG. 4 is a schematic sectional view of the drug delivery device with the control mechanism in the first activating position.

FIGS. 3 and 4 are different views of the drug delivery device 1 with the components as described before. FIG. 3 shows the drug delivery device 1 in a schematic perspective view and FIG. 4 shows a schematic sectional view of the drug delivery device 1.

The activating element 7.1.2 is in a first activating position P2, wherein the activating element 7.2.1 is arranged between the first stop 3.2.1 and the second stop 3.2.2.

The movement of the activating element 7.1.2 from the initial position P1 into the first activating position P2 may be performed by gripping the activating element 7.1.2 manually and pushing it towards the second stop 3.2.2 until the activating element 7.1.2 stops or a resistance is felt by the user. This may be realized with a detent connected to the slot 3.2.

In an alternative embodiment, the activating element 7.1.2 may be in the first activating position P2 when abutting the second stop 3.2.2. In this alternative embodiment, the activating element 7.1.2 is configured as a slidable activating element and a depressible button, wherein the activating element 7.1.2 is moved from the initial position P1 towards the first activating position P2 by depressing the activating element 7.1.2 towards a direction perpendicular to the longitudinal axis A.

Referring again to FIGS. 3 and 4, due to the sliding movement of the activating element 7.1.2 in the slot 3.2, the control element 7.1 rotates with respect to the outer body 3 and to the cartridge 4 around the axis A. The rotational movement of the control element 7.1 and thus of the inner thread 7.1.1 causes a release of the snap connection between the needle cap 2.1 and the outer body 3 and as a result, a removal of the needle cap assembly 2 is allowed by capturing the needle cap 2.1 which is unscrewed from the outer body 3 by moving the activating element 7.1.2 into the first activating position P2.

The drug delivery device 1 is now ready for starting a drug delivery process. The drug delivery device 1 may now be pushed against an injection site, e. g. a patient's skin. For starting the drug delivery, the activating element 7.1.2 has to be moved in a second activating position P3 as illustrated in FIGS. 5 and 6.

Figure 5:
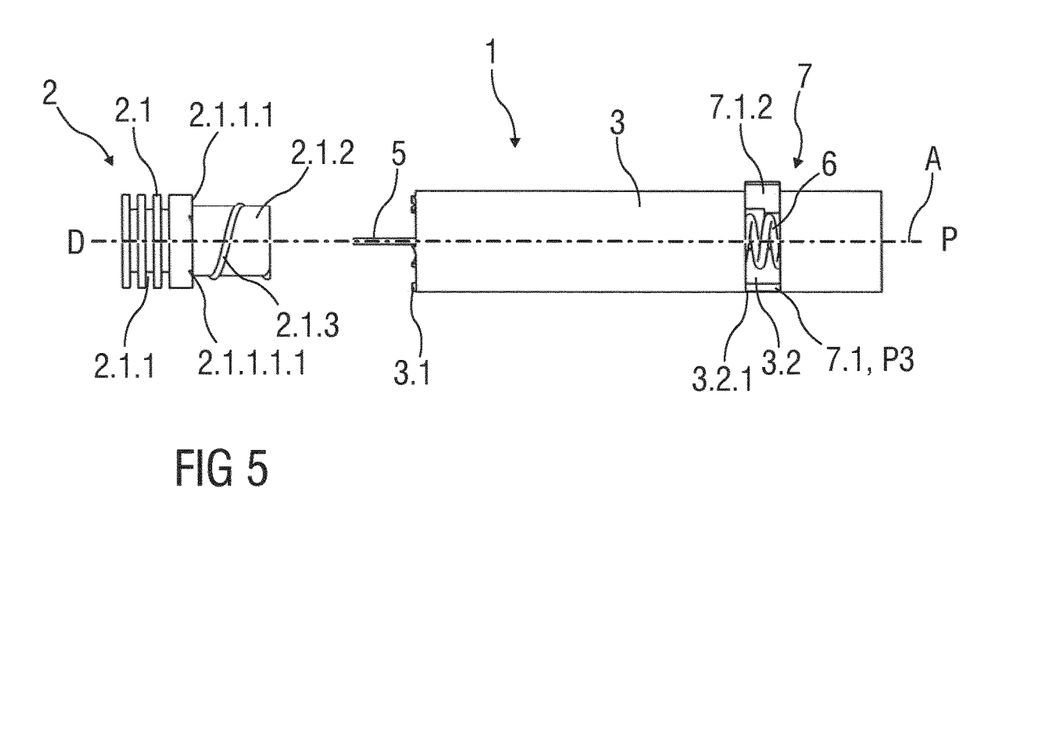
FIG. 5 is an exploded schematic view of the drug delivery device with the control element in a second activating position.
Figure 6:
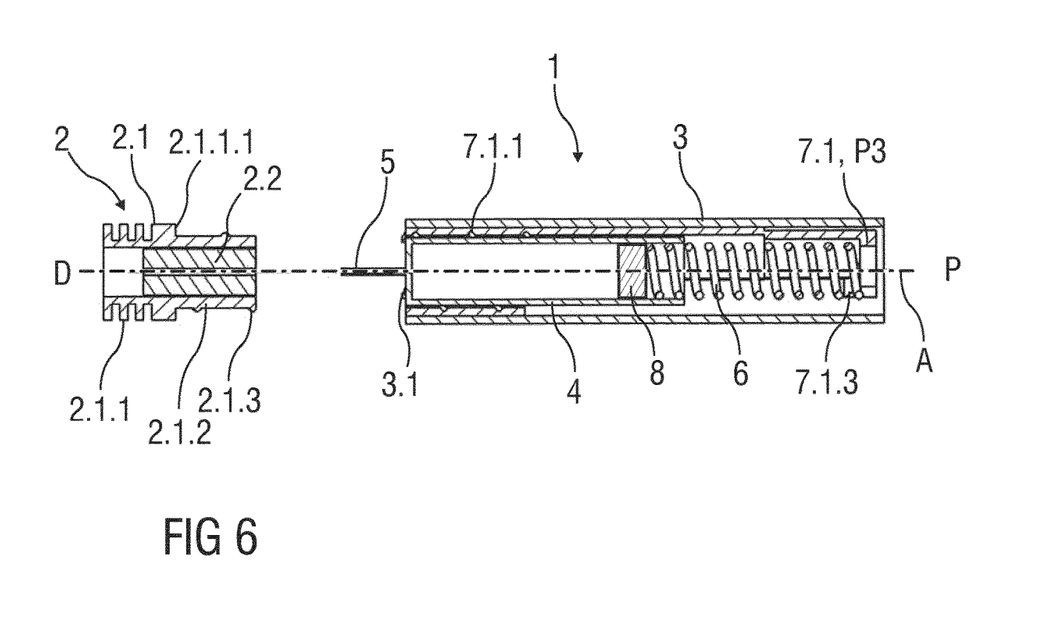
FIG. 6 is a schematic sectional view of the drug delivery device with the control mechanism in the second activating position.

FIGS. 5 and 6 are different views of the drug delivery device 1, wherein the activating element 7.1.2 is in the second activating position P3. FIG. 5 shows a schematic view of the drug delivery device 1 and FIG. 6 shows a schematic longitudinal section of the drug delivery device 1.

In the shown embodiment, the activating element 7.1.2 abuts against the second stop 3.2.2.

In an alternative embodiment, the activating element 7.1.2 may abut the first stop 3.2.1 when arranged in the second activating position P3. Likewise, the activating element 7.1.2 may be configured to be depressed for moving into the second activating position P3.

Referring again to FIGS. 5 and 6, due to the movement of the activating element 7.1.2 towards the second stop 3.2.2, the cartridge 4 is released for moving in the distal direction D with respect to the outer body 3. Thus, the needle 5 is exposed from the outer body 3 for piercing the injection site and drug delivery will start. The release of the cartridge 4 may be performed by a not shown slope on an inner side of the control element 7.1 near a proximal end of the cartridge 4 that pushes the cartridge 4 axially out of the body 3. Afterwards, the spring 6 is activated as it is shown in FIG. 8.

FIG. 7 shows the drug delivery device 1 as described before in a perspective view, wherein the needle cap assembly 2 is released from the drug delivery device 1 and a circular abutting area arranged on the distal end of the control element 7.1 is exposed. The activating element 7.1.2 abuts the second stop 3.2.2 and the needle 5 is still covered by the outer body 3. The control element 7.1 is in the first activating position P2.

Figure 8:
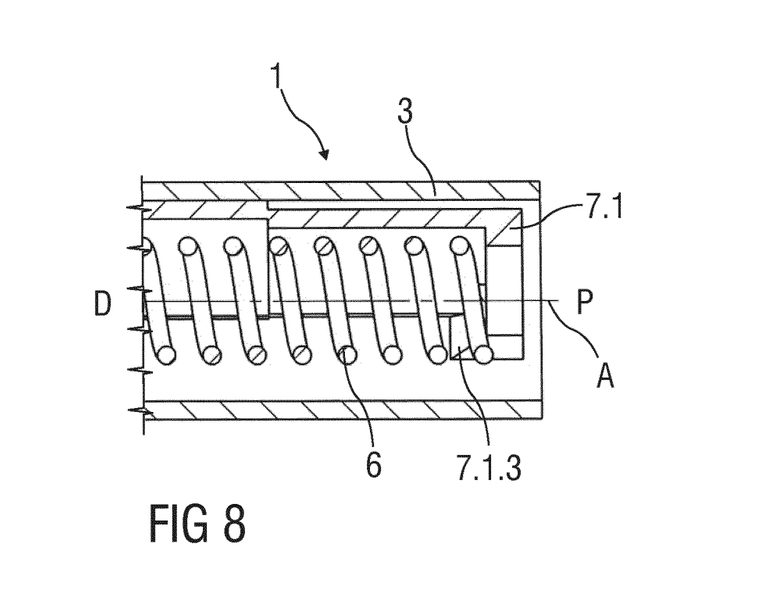
FIG. 8 is an enlarged schematic sectional view of a proximal section of the drug delivery device.

FIG. 8 shows an enlarged schematic longitudinal section of a proximal part of the drug delivery device 1.

The proximal end of the control element 7.1 is coupled to a proximal end of the drive spring 6 and comprises a bevel 7.1.3 for activating a spring force. For example, the drive spring 6 is pre-stressed, thereby biased against the control element 7.1. The spring 6 will be released after passing the bevel 7.1.3 when the control element 7.1 is rotated with respect to the outer body 3. The release of the spring 6 will be realized by mounting the control element 7.1 eccentrically relative to the spring 6 (not shown), thus the spring 6 is blocked by the circumference of the control element 7.1 until the control element 7.1 is in the second activating position P3. In the second activating position P3, the circumference of the control element 7.1 is no longer partially aligned with the spring 6 according to the longitudinal axis A, thus the spring 6 is allowed to relax. Alternatively, there may be an additional part (not shown) which is coupled to the spring 6 and to the control element 7.1 in a manner that the control element 7.1 is rotatable with respect to the additional part. The additional part comprises grooves that correspond with ribs arranged on the inner circumference of the control element 7.1. Depending on the position of the control element 7.1 with respect to the additional part, the additional part is either blocked or released by the ribs of the control element 7.1.

In the illustrated embodiments, the drug delivery device 1 is provided with manual needle insertion and manual drug delivery. Likewise, the drug delivery device 1 could be provided with automatic needle insertion and/or automatic drug delivery.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(w-carboxyheptadecanoyl)-des(B30) human insulin and B29-N-(w-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

LIST OF REFERENCES 1 drug delivery device
2 needle cap assembly
2.1 needle cap
2.1.1 distal portion
2.1.1.1 shoulder
2.1.1.1.1 recess
2.1.2 proximal portion
2.1.3 outer thread
2.2 inner needle shield
3 outer body
3.1 locking projection
3.2 slot
3.2.1 first stop
3.2.2 second stop
4 cartridge
5 needle
6 drive spring
7 control mechanism
7.1 control element
7.1.1 inner thread
7.1.2 activating element
7.1.3 bevel
8 stopper
A longitudinal axis
D distal direction
P proximal direction
P1 initial position
P2 first activating position
P3 second activating position

The invention claimed is:

1. A drug delivery device comprising:
an outer body adapted to receive a cartridge with a needle;
a needle cap assembly adapted to be coupled to the outer body and to cover the needle; and
a control mechanism for activating the drug delivery device, the control mechanism comprises a control element that is received within the outer body and movable relative to the outer body between an initial position, a first activating position, and a second activating position,
wherein the control element is configured to be coupled to the needle cap assembly and to the cartridge,
wherein the needle cap assembly is retained on the outer body when the control element is in the initial position,
wherein the needle cap assembly is configured to be released from the outer body and the needle is configured to be covered by the outer body due to a movement of the control element from the initial position into the first activating position, and
wherein the needle is exposed when the control element is in the second activating position.

2. The drug delivery device according to claim 1, wherein the control element comprises an activating element operable from an outside of the outer body and adapted to move the control element relative to the outer body to subsequently release the needle cap assembly from the outer body and to expose the needle.

3. The drug delivery device according to claim 2, wherein the activating element is configured as a lever.

4. The drug delivery device according to claim 2, wherein the activating element protrudes radially outwards through a slot in a circumference of the outer body.

5. The drug delivery device according to claim 4, wherein the slot is limited by a first stop and a second stop.

6. The drug delivery device according to claim 5, wherein the activating element is guidable within the slot, and wherein the activating element is configured to abut the first stop when the activating element is in the initial position.

7. The drug delivery device according to claim 6, wherein the activating element is located between the first stop and the second stop when the activating element is in the first activating position.

8. The drug delivery device according to claim 6, wherein the activating element is configured to abut the second stop when the activating element is in the second activating position.

9. The drug delivery device according to claim 4, wherein the slot extends in a direction along the circumference of the outer body.

10. The drug delivery device according to claim 4, wherein the control element is configured as an elongate sleeve arranged within the outer body and rotatably movable with respect to the outer body when the activating element is moved within the slot.

11. The drug delivery device according to claim 1, wherein the control element is adapted to be screwed to the needle cap assembly.

12. The drug delivery device according to claim 11, wherein the needle cap assembly comprises an outer thread arranged proximally, and the control element comprises a corresponding inner thread arranged distally.

13. The drug delivery device according to claim 1, wherein the needle cap assembly is rotationally locked to the outer body by a snap connection when the control element is in the initial position.

14. The drug delivery device according to claim 13, wherein the snap connection comprises a number of locking projections on a distal end of the outer body engaging into a number of corresponding recesses on a shoulder of the needle cap assembly.

15. The drug delivery device according to claim 1, wherein the control element is mechanically coupled to a drive spring.

16. The drug delivery device according to claim 1, wherein the outer body comprises the cartridge and the cartridge contains a pharmaceutically active compound.

* * * * *

UNITED STATES PATENT AND TRADEMARK OFFICE
CERTIFICATE OF CORRECTION

| | | |
|---|---|---|
| PATENT NO. | : 10,814,071 B2 | Page 1 of 1 |
| APPLICATION NO. | : 15/743840 | |
| DATED | : October 27, 2020 | |
| INVENTOR(S) | : Stefan Wendland and Michael Harms | |

It is certified that error appears in the above-identified patent and that said Letters Patent is hereby corrected as shown below:

In the Specification

In Column 1, Line 11 (approx.), after "filed" delete "in"

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*